(12) United States Patent
Aoki et al.

(10) Patent No.: US 10,119,173 B2
(45) Date of Patent: Nov. 6, 2018

(54) IONIC LIQUID AND METHOD FOR DISSOLVING CELLULOSE USING THE SAME

(71) Applicant: Panasonic Intellectual Property Management Co., Ltd., Osaka (JP)

(72) Inventors: Takahiro Aoki, Osaka (JP); Tomoko Kawashima, Osaka (JP); Haruka Kusukame, Kyoto (JP); Yuko Taniike, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/671,176

(22) Filed: Aug. 8, 2017

(65) Prior Publication Data

US 2018/0105890 A1    Apr. 19, 2018

(30) Foreign Application Priority Data

Oct. 18, 2016   (JP) .................................. 2016-204304

(51) Int. Cl.
| | |
|---|---|
| C13K 1/02 | (2006.01) |
| C07C 215/08 | (2006.01) |
| C07C 229/26 | (2006.01) |
| C07C 229/36 | (2006.01) |
| C08B 1/00 | (2006.01) |
| C08K 5/00 | (2006.01) |
| D21C 3/20 | (2006.01) |
| D21C 5/00 | (2006.01) |

(52) U.S. Cl.
CPC .............. *C13K 1/02* (2013.01); *C07C 215/08* (2013.01); *C07C 229/26* (2013.01); *C07C 229/36* (2013.01); *C08B 1/00* (2013.01); *C08K 5/00* (2013.01); *D21C 3/20* (2013.01); *D21C 5/00* (2013.01)

(58) Field of Classification Search
CPC ....................................................... C13K 1/02
See application file for complete search history.

(56) References Cited

U.S. PATENT DOCUMENTS

| | | | | |
|---|---|---|---|---|
| 2015/0368371 A1* | 12/2015 | Rogers | ........................ | C08J 3/14 524/13 |
| 2016/0082141 A1* | 3/2016 | Rogers | .................. | A61L 15/225 602/48 |

FOREIGN PATENT DOCUMENTS

| | | |
|---|---|---|
| JP | 2012-144441 | 8/2012 |
| JP | 2015-096255 | 5/2015 |

OTHER PUBLICATIONS

Ning Sun et al., "Understanding pretreatment efficacy of four cholinium and imidazolium ionic liquids by chemistry and computation", Royal Society of Chemistry, Green Chem., 2014, 16, 2546-2557, Jan. 30, 2014.

* cited by examiner

*Primary Examiner* — Melvin C. Mayes
*Assistant Examiner* — Stefanie J Cohen
(74) *Attorney, Agent, or Firm* — McDermott Will & Emery LLP

(57) ABSTRACT

The present invention provides an ionic liquid represented by the following chemical formula, $[(CH_3)_3N(CH_2)_2OH]^+$ $[NH_2(CH_2)_3CH(NH_2)COO]^-$. The present invention provides an ionic liquid capable of dissolving cellulose within twenty-four hours.

14 Claims, 1 Drawing Sheet

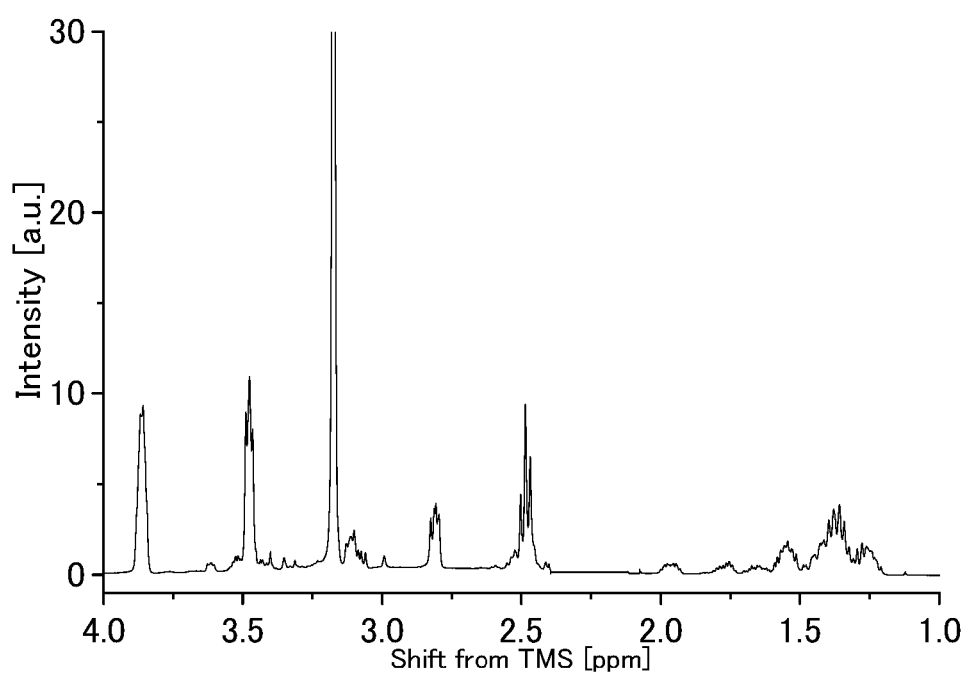

IONIC LIQUID AND METHOD FOR DISSOLVING CELLULOSE USING THE SAME

BACKGROUND

1. Technical Field

The present invention relates to an ionic liquid and a method for dissolving cellulose using the same.

2. Description of the Related Art

Patent Literature 1 discloses using an ionic liquid as an enzyme saccharification pretreatment agent of cellulosic biomass. Patent Literature 1 discloses choline acetate as an ionic liquid in the paragraph [0037]. Furthermore, in the paragraph [0022], Patent Literature 1 discloses that an example of the anion of the ionic liquid is an amino acid anion such as a glutamic acid anion.

Patent Literature 2 discloses an ionic liquid, a purification method of the ionic liquid, and a treatment method of cellulose-based biomass. Patent Literature 2 discloses in the paragraphs [0024]-[0026] that an example of the anion of the ionic liquid is an amino acid anion such as alanine, lysine, threonine, isoleucine, asparagine, valine, phenylalanine, tyrosine, methionine, leucine, or ornithine.

Non Patent Literature 1 discloses decomposition of cellulose using a cellulolytic enzyme with the decomposition accelerator of an ionic liquid consisting of $[(CH_3)_3NCH_2CH_2OH]^+[NH_2(CH_2)_4CH(NH_2)COO]^-$ (hereinafter, referred to as "[Ch][Lys]").

CITATION LIST

Patent Literature 1
Japanese patent laid-open publication No. 2015-096255A
Patent Literature 2
Japanese patent laid-open publication No. 2012-144441A
Non Patent Literature 1
Ning Sun et. al., "Understanding pretreatment efficacy of four cholinium and imidazolium ionic liquids by chemistry and computation", Royal Society of Chemistry, Green Chem., 2014, 16, 2546-2557

SUMMARY

The present invention provides an ionic liquid represented by the following chemical formula (I).

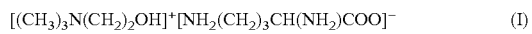

$$[(CH_3)_3N(CH_2)_2OH]^+[NH_2(CH_2)_3CH(NH_2)COO]^- \quad (I)$$

The present invention provides an ionic liquid capable of dissolving cellulose within twenty-four hours.

BRIEF DESCRIPTION OF THE DRAWING

FIGURE shows a result of the nuclear magnetic resonance spectrum $^1$H-NMR measurement in the inventive example 1.

DETAILED DESCRIPTION OF THE EMBODIMENT

Hereinafter, an embodiment of the present invention will be described. The ionic liquid according to the present embodiment is in a liquid state at 150 degrees Celsius or less and represented by the following chemical formula (I).

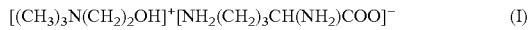

$$[(CH_3)_3N(CH_2)_2OH]^+[NH_2(CH_2)_3CH(NH_2)COO]^- \quad (I)$$

Cellulose is added to the ionic liquid according to the present embodiment. Desirably, the cellulose has weight average molecular weight of not less than 30,000. Desirably, the cellulose has weight average molecular weight of not more than 500,000.

As well known, an ionic liquid is composed of a cation and an anion. In the present embodiment, the cation is a choline cation represented by the chemical formula $[(CH_3)_3N(CH_2)_2OH]^+$ (hereinafter, referred to as "[2-HETMA]"). Choline is an aqueous nutrient essential for a human. In the present embodiment, the anion is an ornithine anion represented by the chemical formula $[NH_2(CH_2)_3CH(NH_2)COO]^-$ (hereinafter, referred to as "[Orn]"). Ornithine is one kind of amino acids. For simple expression, the ionic liquid according to the present embodiment may be referred to as [2-HETMA][Orn].

[2-HETMA] and [Orn] exist in a human body, and are materials having high safety for a living body for the reason of holding of metabolic pathway in a body and other reasons.

In addition, for the reason that hydrogen bonding strength of an amino group or a carboxyl group derived from ornithinate is greater than hydrogen bonding strength of OH groups between cellulose chains and other reasons, the ionic liquid according to the present disclosure is capable of weaking hydrogen bonds between the cellulose chains and the effect of improving solubility of cellulose is expected.

The ionic liquid according to the present embodiment may be synthesized on the basis of the following chemical reaction formula (II). As shown in the following chemical reaction formula (II), choline is mixed with ornithine hydrochloride. The molar quantity of choline is twice as much as that of ornithine hydrochloride. The mixture solution containing choline and ornithine is heated under vacuum, and then dried to provide the ionic liquid according to the present embodiment through dehydration reaction between the hydroxyl ion of choline and the hydrogen ion of the carboxyl group of the ornithine.

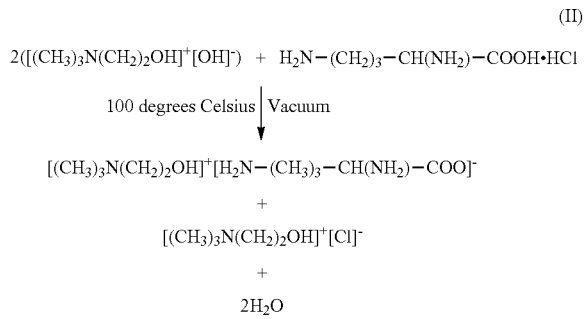

As is clear from the inventive examples and the comparative examples which will be described later, the ionic liquid according to the present embodiment dissolves cellulose more quickly than an ionic liquid consisting of the choline cation and another amino acid anion. As one embodiment, the ionic liquid according to the present embodiment dissolves cellulose within twenty-four hours after the cellulose is added to the ionic liquid according to the present embodiment. Unlike the disclosure of Non Patent Literature 1, a cellulolytic enzyme is not necessary in the present embodiment.

It is desirable that the ionic liquid to which the cellulose has been added is heated in order to promote the dissolution. As one embodiment, the ionic liquid to which the cellulose has been added is heated at a temperature of not less than 70 degrees Celsius and not more than 100 degrees Celsius at a pressure of not less than 0.01 MPa and not more than 0.1 MPa for twenty-four hours.

The ionic liquid to which the cellulose has been added may be left at rest until the cellulose is dissolved in the ionic liquid. The ionic liquid to which the cellulose has been added may be stirred.

A kind of the cellulose dissoluble in the ionic liquid of the present disclosure is not limited particularly. For example, native cellulose derived from plant species, native cellulose derived from living organisms, or artificial cellulose such as regenerated cellulose like cellophane, or cellulose nanofiber may be applied. In addition, it does not depend on the crystalline state of original cellulose. In other words, it is known that cellulose has a I-type-IV-type crystalline structure or a non-crystalline structure. Cellulose having any structure may be dissolved.

The ionic liquid composition according to the present embodiment may contain the ionic liquid and other components. An example of the other components is water or an aprotic polar solvent. The ionic liquid composition according to the present embodiment is in a liquid state.

As described above, the ionic liquid composition according to the present embodiment may contain water. In the ionic liquid composition, the weight ratio of the water to the ionic liquid may be not more than 4.3%. See the inventive examples 2-3 and the comparative examples 25-28 which will be described later.

As described above, the ionic liquid composition according to the present embodiment may contain an aprotic polar solvent in order to control a viscosity thereof. An example of the aprotic polar solvent is dimethyl sulfoxide. In the ionic liquid composition, the weight ratio of the ionic liquid to the aprotic polar solvent may be not less than 309%.

Unlike the disclosure of Non Patent Literature 1, the ionic liquid composition according to the present embodiment need not contain cellulolytic enzyme.

EXAMPLES

Hereinafter, the present invention will be described in more detail with reference to the following examples.

Inventive Example 1

L-ornithine hydrochloride (available from Wako Pure Chemical Industries, Ltd., 8.4 grams, 50 millimoles) was mixed with a choline aqueous solution (available from Tokyo Chemical Industry Co., Ltd., 24.7 grams, 100 millimoles) to provide a mixture solution. The mixture solution was dried at a temperature of 100 degrees Celsius under reduced pressure for three hours. In this way, an ionic liquid composition containing [2-HETMA][Orn] ionic liquid was obtained. The weight of the obtained ionic liquid composition was 15.3 grams. The yield was 85%. The by-product was choline chloride.

The obtained [2-HETMA][Orn] ionic liquid composition was confirmed by using nuclear magnetic resonance spectrum measurement. Please note that the structure of the ionic liquid composition fabricated in the present example were determined with a nuclear magnetic resonance spectrum (measured with Unity Inova-400 made by Varian Inc., 400 MHz: $^1$H-NMR). The measurement was conducted using deuterated DMSO and indicated with δ value (ppm) when tetramethyl silane (i.e., TMS) was an internal standard. FIGURE shows a result of the nuclear magnetic resonance spectrum $^1$H-NMR measurement in the inventive example 1.

In addition, a water amount contained in the [2-HETMA][Orn] ionic liquid composition (5 grams) was measured by Karl Fischer's method. In this method, the weight of the [2-HETMA][Orn] ionic liquid composition was measured three times to calculate the average weight thereof, and then this ionic liquid composition was injected to a moisture measurement device CA-100 (available from Mitsubishi Chemical Analytech Co., Ltd.). The weight of the residual moisture was measured and a water ratio was calculated by dividing by the weight of the ionic liquid composition. As a result, the water amount of the [2-HETMA][Orn] ionic liquid composition was 1.32% (0.66 grams).

The [2-HETMA][Orn] ionic liquid composition having a weight of 0.97 grams was supplied to a glass bottle. Cellulose (0.03 grams, available from Sigma-Aldrich, trade name: Avicel PH-101, average molecular weight measured by a gel-permeation chromatography-multi angle light scattering method: approximately 30,000) was added to the glass bottle. The solution was stored at a temperature of 90 degrees Celsius at a pressure of 0.02 MPa. The present inventors observed visually whether or not the added cellulose was dissolved in the [2-HETMA][Orn] ionic liquid composition. As a result, after five hours elapsed from the mixture of the ionic liquid composition and the cellulose, the cellulose was dissolved in the [2-HETMA][Orn] ionic liquid composition. Furthermore, as a basis that the peak derived from the crystalline property of the cellulose disappeared in the X-ray diffraction analysis result, the present inventors also confirmed the dissolution of the cellulose.

Inventive Example 2

In the inventive example 2, an experiment similar to the inventive example 1 was conducted, except of using bleached pulp made from wood (average molecular weight: approximately 300,000-500,000) as cellulose. The average molecular weight was calculated similarly to that of inventive example 1.

Comparative Example 1

In the comparative example 1, an experiment similar to the inventive example 1 was conducted, except of using pyruvic acid (hereinafter, referred to as "[Pyr]", available from Tokyo Chemical Industry Co., Ltd., 8.8 grams, 100 millimoles) in place of L-ornithine hydrochloride.

Comparative Example 2

In the comparative example 2, an experiment similar to the inventive example 1 was conducted, except of using lactic acid (hereinafter, referred to as "[Lac]", available from Tokyo Chemical Industry Co., Ltd., 9.0 grams, 100 millimoles) in place of L-ornithine hydrochloride.

Comparative Example 3

In the comparative example 3, an experiment similar to the inventive example 1 was conducted, except of using glycine (hereinafter, referred to as "[Gly]", available from Tokyo Chemical Industry Co., Ltd., 7.5 grams, 100 millimoles) in place of L-ornithine hydrochloride.

Comparative Example 4

In the comparative example 4, an experiment similar to the inventive example 1 was conducted, except of using α-alanine (hereinafter, referred to as "[Ala]", available from Tokyo Chemical Industry Co., Ltd., 8.9 grams, 100 millimoles) in place of L-ornithine hydrochloride. The cellulose was not dissolved.

Comparative Example 5

In the comparative example 5, an experiment similar to the inventive example 1 was conducted, except of using histidine (hereinafter, referred to as "[His]", available from Tokyo Chemical Industry Co., Ltd., 15.5 grams, 100 millimoles) in place of L-ornithine hydrochloride.

Comparative Example 6

In the comparative example 6, an experiment similar to the inventive example 1 was conducted, except of using arginine (hereinafter, referred to as "[Arg]", available from Tokyo Chemical Industry Co., Ltd., 8.7 grams, 100 millimoles) in place of L-ornithine hydrochloride.

Comparative Example 7

In the comparative example 7, an experiment similar to the inventive example 1 was conducted, except of using valine (hereinafter, referred to as "[Val]", available from Tokyo Chemical Industry Co., Ltd., 11.7 grams, 100 millimoles) in place of L-ornithine hydrochloride.

Comparative Example 8

In the comparative example 8, an experiment similar to the inventive example 1 was conducted, except of using leucine (hereinafter, referred to as "[Leu]", available from Tokyo Chemical Industry Co., Ltd., 13.1 grams, 100 millimoles) in place of L-ornithine hydrochloride.

Comparative Example 9

In the comparative example 9, an experiment similar to the inventive example 1 was conducted, except of using phenylalanine (hereinafter, referred to as "[Phe]", available from Tokyo Chemical Industry Co., Ltd., 16.5 grams, 100 millimoles) in place of L-ornithine hydrochloride.

Comparative Example 10

In the comparative example 10, an experiment similar to the inventive example 1 was conducted, except of using tyrosine (hereinafter, referred to as "[Tyr]", available from Tokyo Chemical Industry Co., Ltd., 18.1 grams, 100 millimoles) in place of L-ornithine hydrochloride.

Comparative Example 11

In the comparative example 11, an experiment similar to the inventive example 1 was conducted, except of using tryptophan (hereinafter, referred to as "[Trp]", available from Tokyo Chemical Industry Co., Ltd., 20.4 grams, 100 millimoles) in place of L-ornithine hydrochloride.

Comparative Example 12

In the comparative example 12, an experiment similar to the inventive example 1 was conducted, except of using proline (hereinafter, referred to as "[Pro]", available from Tokyo Chemical Industry Co., Ltd., 11.5 grams, 100 millimoles) in place of L-ornithine hydrochloride.

Comparative Example 13

In the comparative example 13, an experiment similar to the inventive example 1 was conducted, except of using serine (hereinafter, referred to as "[Ser]", available from Tokyo Chemical Industry Co., Ltd., 10.5 grams, 100 millimoles) in place of L-ornithine hydrochloride.

Comparative Example 14

In the comparative example 14, an experiment similar to the inventive example 1 was conducted, except of using glutamine (hereinafter, referred to as "[Gln]", available from Tokyo Chemical Industry Co., Ltd., 14.6 grams, 100 millimoles) in place of L-ornithine hydrochloride.

Comparative Example 15

In the comparative example 15, an experiment similar to the inventive example 1 was conducted, except of using methionine (hereinafter, referred to as "[Met]", available from Tokyo Chemical Industry Co., Ltd., 14.9 grams, 100 millimoles) in place of L-ornithine hydrochloride.

Comparative Example 16

In the comparative example 16, an experiment similar to the inventive example 1 was conducted, except of using glutamic acid (hereinafter, referred to as "[Glu]", available from Tokyo Chemical Industry Co., Ltd., 7.4 grams, 50 millimoles) in place of L-ornithine hydrochloride. In a case where 100 millimoles of glutamic acid was used, the mixture was solidified. For this reason, an ionic liquid composition was not obtained.

Comparative Example 17

In the comparative example 17, an experiment similar to the inventive example 1 was conducted, except of using isoleucine (hereinafter, referred to as "[Ile]", available from Tokyo Chemical Industry Co., Ltd., 13.1 grams, 100 millimoles) in place of L-ornithine hydrochloride.

Comparative Example 18

In the comparative example 18, an experiment similar to the inventive example 1 was conducted, except of using asparagine (hereinafter, referred to as "[Asn]", available from Tokyo Chemical Industry Co., Ltd., 13.2 grams, 100 millimoles) in place of L-ornithine hydrochloride.

Comparative Example 19

In the comparative example 19, an experiment similar to the inventive example 1 was conducted, except of using aspartic acid (hereinafter, referred to as "[Asp]", available from Tokyo Chemical Industry Co., Ltd., 6.7 grams, 50 millimoles) in place of L-ornithine hydrochloride. In a case where 100 millimoles of aspartic acid was used, the mixture was solidified. For this reason, an ionic liquid composition was not obtained.

Comparative Example 20

In the comparative example 20, an experiment similar to the inventive example 1 was conducted, except of using cysteine (hereinafter, referred to as "[Cys]", available from Tokyo Chemical Industry Co., Ltd., 12.1 grams, 100 millimoles) in place of L-ornithine hydrochloride.

Comparative Example 21

In the comparative example 21, an experiment similar to the inventive example 1 was conducted, except of using threonine (hereinafter, referred to as "[Thr]", available from Tokyo Chemical Industry Co., Ltd., 11.9 grams, 100 millimoles) in place of L-ornithine hydrochloride.

Comparative Example 22

In the comparative example 22, an experiment similar to the inventive example 1 was conducted, except of using acetic acid (hereinafter, referred to as "[Ac]", available from Tokyo Chemical Industry Co., Ltd., 6.0 grams, 100 millimoles) in place of L-ornithine hydrochloride.

Comparative Example 23

In the comparative example 23, an experiment similar to the inventive example 1 was conducted, except of using tartaric acid (hereinafter, referred to as "[Tar]", available from Tokyo Chemical Industry Co., Ltd., 7.5 grams, 50 millimoles) in place of L-ornithine hydrochloride. In a case where 100 millimoles of tartaric acid was used, the mixture was solidified. For this reason, an ionic liquid composition was not obtained.

Comparative Example 24

In the comparative example 24, an experiment similar to the inventive example 1 was conducted, except of using citric acid (hereinafter, referred to as "[Cit]", available from Tokyo Chemical Industry Co., Ltd., 6.4 grams, 33 millimoles) in place of L-ornithine hydrochloride. In a case where 100 or 50 millimoles of citric acid was used, the mixture was solidified. For this reason, an ionic liquid composition was not obtained.

The following table 1 shows the results of the above examples.

TABLE 1

|  | Composition | Result |
| --- | --- | --- |
| Inventive example 1 | [2-HETMA] [Orn] | Dissolved in 5 hours after the mixture. |
| Inventive example 2 | [2-HETMA] [Orn] | Dissolved in 20 hours after the mixture. |
| Comparative example 1 | [2-HETMA] [Pyr]] | Not dissolved even after 24 hours elapsed from the mixture |
| Comparative example 2 | [2-HETMA] [Lac] | |
| Comparative example 3 | [2-HETMA] [Gly] | |
| Comparative example 4 | [2-HETMA] [Ala] | |
| Comparative example 5 | [2-HETMA] [His] | |
| Comparative example 6 | [2-HETMA] [Arg] | |
| Comparative example 7 | [2-HETMA] [Val] | |

TABLE 1-continued

|  | Composition | Result |
| --- | --- | --- |
| Comparative example 8 | [2-HETMA] [Leu] | |
| Comparative example 9 | [2-HETMA] [Phe] | |
| Comparative example 10 | [2-HETMA] [Tyr] | |
| Comparative example 11 | [2-HETMA] [Trp] | |
| Comparative example 12 | [2-HETMA] [Pro] | |
| Comparative example 13 | [2-HETMA] [Ser] | |
| Comparative example 14 | [2-HETMA] [Gln] | |
| Comparative example 15 | [2-HETMA] [Met] | |
| Comparative example 16 | [2-HETMA] [Glu] | |
| Comparative example 17 | [2-HETMA] [Ile] | |
| Comparative example 18 | [2-HETMA] [Asn] | |
| Comparative example 19 | [2-HETMA] [Asp] | |
| Comparative example 20 | [2-HETMA] [Cys] | |
| Comparative example 21 | [2-HETMA] [Thr] | |
| Comparative example 22 | [2-HETMA] [Ac] | |
| Comparative example 23 | [2-HETMA] [Tar] | |
| Comparative example 24 | [2-HETMA] [Cit] | |

As is clear from Table 1, when the ionic liquid represented by [2-HETMA][Orn] is used, the cellulose is dissolved in the ionic liquid composition within twenty-four hours after the mixture of the ionic liquid composition and the cellulose. On the other hand, the cellulose is not dissolved in the ionic liquid composition even after twenty-four hours, when other amino acid anions are used. As just described, when the ionic liquid represented by [2-HETMA][Orn] is used, the cellulose is dissolved quickly within twenty-four hours.

Inventive Example 3

In the inventive example 3, an experiment similar to the inventive example 2 was conducted, except that 10 grams of the ionic liquid composition according to the inventive example 1 further contained water (0.3 grams, 4.32 weight percent) and that the solution to which the cellulose had been added was sealed and stored at 90 degrees Celsius and at normal pressures.

Comparative Example 25

In the comparative example 25, an experiment similar to the inventive example 2 was conducted, except that 10 grams of the ionic liquid composition according to the inventive example 1 further contained water (0.5 grams, 6.32 weight percent) and that the solution to which the cellulose had been added was sealed and stored at 90 degrees Celsius and at normal pressures.

Comparative Example 26

In the comparative example 26, an experiment similar to the inventive example 2 was conducted, except that 10 grams of the ionic liquid composition according to the inventive example 1 further contained water (0.6 grams, 7.32 weight percent) and that the solution to which the cellulose had been added was sealed and stored at 90 degrees Celsius and at normal pressures.

Comparative Example 27

In the comparative example 27, an experiment similar to the inventive example 2 was conducted, except that 10 grams of the ionic liquid composition according to the inventive example 1 further contained water (0.7 grams, 8.32 weight percent) and that the solution to which the cellulose had been added was sealed and stored at 90 degrees Celsius and at normal pressures.

Comparative Example 28

In the comparative example 28, an experiment similar to the inventive example 2 was conducted, except that 10 grams of the ionic liquid composition according to the inventive example 1 further contained water (1.0 gram, 11.32 weight percent) and that the solution to which the cellulose had been added was sealed and stored at 90 degrees Celsius and at normal pressures.

The following Table 2 shows the results of the above examples.

TABLE 2

| | Composition | Water amount (weight %) | Result |
|---|---|---|---|
| Inventive example 2 | [2-HETMA][Orn] | 1.32 | Dissolved in 20 hours after the mixture |
| Inventive example 3 | | 4.32 | Dissolved in 20 hours after the mixture |
| Comparative example 25 | | 6.32 | Dissolved in 30 hours after the mixture |
| Comparative example 26 | | 7.32 | Dissolved in 41 hours after the mixture |
| Comparative example 27 | | 8.32 | Not dissolved in 100 hours after the mixture |
| Comparative example 28 | | 11.32 | Not dissolved in 100 hours after the mixture |

As is clear from Table 2, when the water amount is not more than 4.32 weight percent, the cellulose is dissolved in the ionic liquid composition within twenty-four hours after the mixture of the ionic liquid composition and the cellulose. On the other hand, when the water amount is not less than 6.32 weight percent, the cellulose is not dissolved in the ionic liquid composition within twenty-four hours.

Inventive Example 4

In the inventive example 4, dimethyl sulfoxide (hereinafter, referred to as "DMSO", 1.00 gram, the weight ratio thereof to the ionic liquid [2-HETMA][Orn]: 103%) was added to the [2-HETMA][Orn] ionic liquid composition (1.0 gram) in which the cellulose had been dissolved (namely, the [2-HETMA][Orn] ionic liquid composition which was obtained in the inventive example 2 and contained the cellulose). Then, this solution was sealed and stored at a temperature of 90 degrees Celsius at normal pressures. The present inventors observed whether or not the cellulose was precipitated.

Inventive Example 5

In the inventive example 5, an experiment similar to the inventive example 4 was conducted, except of addition of 2.00 grams of DMSO (the weight ratio thereof to the ionic liquid [2-HETMA][Orn]: 206%).

Inventive Example 6

In the inventive example 6, an experiment similar to the inventive example 4 was conducted, except of addition of 3.00 grams of DMSO (the weight ratio thereof to the ionic liquid [2-HETMA][Orn]: 309%).

Comparative Example 29

In the comparative example 29, an experiment similar to the inventive example 4 was conducted, except of addition of 4.00 grams of DMSO (the weight ratio thereof to the ionic liquid [2-HETMA][Orn]: 412%).

The following Table 3 shows the results of the above examples.

TABLE 3

| | Weight ratio of DMSO to [2-HETMA] [Orn] | Result |
|---|---|---|
| Inventive example 4 | 103 | Cellulose was not precipitated. |
| Inventive example 5 | 206 | Cellulose was not precipitated. |
| Inventive example 6 | 309 | Cellulose was not precipitated. |
| Comparative example 29 | 412 | Cellulose was precipitated. |

As is clear from Table 3, when the weight ratio of the DMSO to the ionic liquid represented by [2-HETMA][Orn] was not more than 309%, the cellulose was not precipitated even after twenty-four hours. On the other hand, when the weight ratio of the DMSO to the ionic liquid represented by [2-HETMA][Orn] was not less than 412%, the cellulose was precipitated within twenty-four hours. As just described, when the weight ratio of the DMSO to the ionic liquid composition represented by [2-HETMA][Orn] was not more than 309%, the cellulose was not precipitated even after twenty-four hours.

INDUSTRIAL APPLICABILITY

The ionic liquid according to the present embodiment can be used for dissolution of cellulose within twenty-four hours.

The invention claimed is:

1. A method for dissolving cellulose, the method comprising:
   (a) adding cellulose to ionic liquid represented by the following chemical formula (I):

$[(CH_3)_3N(CH_2)_2OH]^+[NH_2(CH_2)_3CH(NH_2)COO]^-$ (I).

2. The method according to claim 1, further comprising:
   (b1) heating the ionic liquid to which the cellulose has been added to dissolve the cellulose in the ionic liquid after the step (a).

3. The method according to claim 1, further comprising:
   (b2) leaving the ionic liquid to which the cellulose has been added at rest to dissolve the cellulose in the ionic liquid after the step (a).

4. The method according to claim 1, further comprising:
   (b3) stirring the ionic liquid to which the cellulose has been added to dissolve the cellulose in the ionic liquid after the step (a).

5. The method according to claim 1, wherein cellulose is dissolved in the ionic liquid within twenty-four hours after the step (a).

6. A method for dissolving cellulose, the method comprising:
   (a) adding cellulose to an ionic liquid composition containing an ionic liquid represented by the following chemical formula (I):

$[(CH_3)_3N(CH_2)_2OH]^+[NH_2(CH_2)_3CH(NH_2)COO]^-$ (I).

7. The method according to claim 6, further comprising:
(b1) heating the ionic liquid composition to which the cellulose has been added to dissolve the cellulose in the ionic liquid after the step (a).

8. The method according to claim 6, further comprising:
(b2) leaving the ionic liquid composition to which the cellulose has been added at rest to dissolve the cellulose in the ionic liquid after the step (a)'.

9. The method according to claim 6, further comprising:
(b3) stirring the ionic liquid composition to which the cellulose has been added to dissolve the cellulose in the ionic liquid after the step (a).

10. The method according to claim 6, wherein the cellulose is dissolved in the ionic liquid composition within twenty-four hours after the step (a).

11. The method according to claim 6, wherein the ionic liquid composition contains water, and weight ratio of the water to the ionic liquid is not more than 4.3%.

12. The method according to claim 6, wherein the ionic liquid composition contains an aprotic polar solvent.

13. The method according to claim 12, wherein the aprotic polar solvent is dimethyl sulfoxide.

14. The method according to claim 13, wherein weight ratio of the dimethyl sulfoxide to the ionic liquid is not more than 309%.

* * * * *